United States Patent [19]

Gizur et al.

[11] Patent Number: 5,225,416
[45] Date of Patent: Jul. 6, 1993

[54] 1,2,3,6-TETRAHYDROPYRIDINE DERIVATIVES USEFUL FOR IMPROVING CEREBRAL BLOOD CIRCULATION

[75] Inventors: Tibor Gizur; Kálmän Harsányi, both of Budapest; Attila Csehi, Göd; Anikó Demeter née Szabó; Ferenc Trischler, both of Budapest; Éva Vajda, Dorog; László Szporny, Budapest; Béla Kiss, Budapest; Egon Kárpáti, Budapest; Éva Pálosi, Budapest; Zsolt Szombathelyi, Budapest; Ádám Sarkadi, Budapest; Anikó Gere, Budapest; Mihály Bodó, Budapest; Katalin Csomor, Budapest; Judit Laszy, Budapest; Zsolt Szentirmai, Budapest; Erzsébet Lapis, Budapest; Sándor Szabó, Budapest, all of Hungary

[73] Assignee: Richter Gedeon Vegyeszeti Termekek Gyara Rt., Budapest, Hungary

[21] Appl. No.: 805,861

[22] Filed: Dec. 10, 1991

[30] Foreign Application Priority Data

Dec. 13, 1990 [HU] Hungary ............................... 8253/90

[51] Int. Cl.$^5$ .................... C07D 211/70; A61K 31/44
[52] U.S. Cl. .................................. 514/277; 546/339; 546/340; 546/344
[58] Field of Search ...................... 546/339, 340, 344; 514/277

[56] References Cited

U.S. PATENT DOCUMENTS 4,645,771  2/1987  Mills .................................... 514/277

OTHER PUBLICATIONS

March, Advanced Organic Chemistry, Second Edition pp. 108-112, 829-834 McGraw Hill Pub. 1979.

Primary Examiner—Alan L. Rotman
Attorney, Agent, or Firm—Herbert Dubno

[57] ABSTRACT

The present invention relates to novel 1,2,3,6-tetrahydropyridine derivatives of the general formula (I)

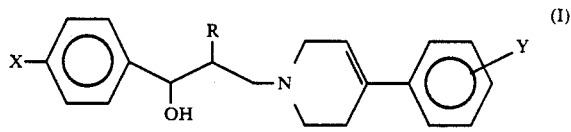

wherein
R stands for hydrogen or an alkyl group,
X stands for an unsubstituted phenyl or benzyl group or for a phenyl or benzyl group substituted with a halogen atom,
Y stands for hydrogen or halogen or a trifluoromethyl group as well as enantiomers acid addition salts thereof.

The invention further extends to pharmaceutical compositions containing said compounds as active ingredient mainly for improving cerebral blood circulation and antihypoxic activity. The 1,2,3,6-tetrahydropyridine derivatives of the general formula (I) are prepared by treating an oxo derivative of the general formula (II)

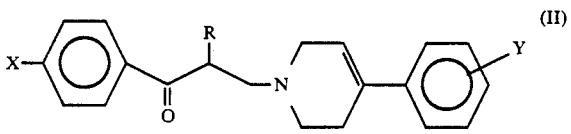

wherein R, X and Y are as given above in an organic solvent by a reducing agent and reacting the obtained 1,2,3,6-tetrahydropyridine derivative of the general formula (I), wherein R, X and Y are as given above, with a mineral or organic acid and converting the same, if desired, to an acid addition salt.

27 Claims, No Drawings

1,2,3,6-TETRAHYDROPYRIDINE DERIVATIVES USEFUL FOR IMPROVING CEREBRAL BLOOD CIRCULATION

FIELD OF THE INVENTION

The present invention is directed to novel 1,2,3,6-tetrahydropyridine-derivatives of the formula (I)

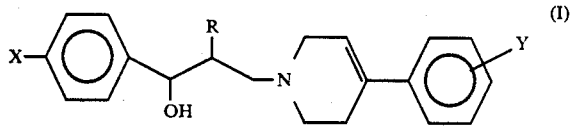

wherein
R stands for hydrogen or an alkyl group,
X stands for an unsubstituted phenyl or benzyl group or for a phenyl or benzyl group substituted with a halogen atom,
Y stands for hydrogen or halogen or a trifluoromethyl group as well as enantiomers and/or acid addition salts thereof. The invention further relates to pharmaceutical compositions containing as active ingredient the 1,2,3,6-tetrahydropyridine derivatives mentioned above having a cerebral blood circulation improving and antihypoxic effect and the present invention also provides a process for the preparation of said compounds and pharmaceutical compositions. The invention also extends to the methods of treatment in the course of which an efficient amount of 1,2,3,6-tetrahydropyridine derivatives or acid addition salts thereof is administered to mammals including humans in order to improve the blood circulation in the brain, in order to produce antihypoxic effects and to influence memory disturbances caused by hypoxia.

The alkyl group as used hereinafter in the specification stands for straight- or branched-chain alkyl groups containing 1 to 10 carbon atoms. As an example methyl, ethyl, n- and isopropyl, n- and iso- and sec.- and tert.-butyl group and the various pentyl-, hexyl-, heptyl-, octyl-, nonyl- and decyl-groups can be mentioned. The preferred representatives of the alkyl groups contain 1 to 6, most preferably 1 to 4 carbon atoms. The latter groups are indicated as lower alkyl groups in the disclosure.

Halogen atom can be a fluorine, chlorine, bromine and iodine atom.

DESCRIPTION OF THE INVENTION

According to the present invention 1,2,3,6-tetrahydropyridine derivatives of the formula (I) and/or enantiomers thereof can be prepared by treating an oxo derivative of the formula (II)—wherein R, X and Y are as given above

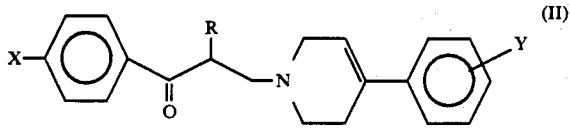

with a reducing agent in an organic solvent and the obtained 1,2,3,6-tetrahydropyridine derivative of the formula (I)—wherein R, X and Y are as given above—is, if desired, reacted with a mineral or organic acid and the obtained compound is converted to an acid addition salt and/or if desired resolved to enantiomers.

As a reducing agent a complex metal hydride, preferably sodium-[tetrahydrido-borate] can be used. The reduction can also be performed under the conditions of Meerwein-Ponndorf-Verley reduction [Ann. Chem., 444, 221. (1926); Angew. Chem., 39, 138. (1926)], e.g. in isopropanol by using an aluminum alkoxide.

The oxo derivatives of the formula (II) are also novel. They can be prepared by a chemical reaction known per se by reacting an 1,2,3,6-tetrahydropyridine derivative containing in the 4-position a phenyl group carrying an Y substituted with a suitably substituted aceto- or propiophenone derivative in the presence of formaldehyde under the conditions of Mannich-reaction [Arch. Pharm., 250, 647. (1912)].

The reduction of the oxo derivative of the formula (II) with sodium [tetrahydrido borate] is carried out in the base form of the compound to be reduced in a lower alkanol or a mixture of such alcanol and acetonitrile under stirring at a temperature of 20° to 50° C. The reaction is monitored by thin layer chromatography.

The oxo derivatives of the formula (II) can be liberated with inorganic bases from the acid addition salts thereof.

The reduction according to Merwein-Ponndorf-Verley can be performed in isopropanol by using aluminum isopropylate. The reduction can be conducted preferably at a temperature corresponding to the boiling point of the reaction mixture.

The compounds of the formula (I) prepared according to the invention can be isolated by pouring the reaction mixture into water followed by filtration. The end-product can be purified by recrystallization from a lower alkanol. The compounds of the formula (I) obtained in the form of a free base can be converted, if desired, to acid addition salt by reacting same with an inorganic or organic acid, by using the conventional methods for salt formation. Acid addition salts formed with hydrochloric acid are preferred.

The structure of the compounds of the formula (I) is proved unambiguously by spectroscopic data.

The biological effect of the compounds according to the invention are shown by the following tests.

Male (CFLP LATI) mice weighing 24–26 g and male spontaneous hypertensive rats (SHR) weighing 160–180 g were used as test animals. The test compounds were administered orally in a volume of 10 ml/kg 1 hour before the test.

ANTIHYPOXIC EFFECT IN MICE

1. Anoxic asphyxia

The mice were treated after 16 hours fasting with the oral dosage of the test compounds. 1 hour after the treatment the animals were placed to 100 ml sealed glasses and the survival time of the animals was measured. The groups consisting of 10 animals and treated with the test compounds were considered protected if the average survival time was by 30 percent longer than the survival of the group treated with placebo. From the percentage of the surviving animals the 50% effective dosage ($ED_{50}$) was calculated by probit analysis.

2. Hypobaric hypoxia (HH)

After 16 hours of fasting and 1 hour of pretreatment the animals were placed to a 6-liter exsiccator and the pressure was reduced within 20 seconds to 22.66 kPa (170 Hgmm), and from this time on the survival time was measured until the last breathing movement. Animals surviving by 100% longer than the average survival of the control group were considered as protected.

3. Cytotoxic hypoxia (KCN)

The animals were treated after 1 hour pretreatment with an i.v. dosage of 5 mg/kg potassium cyanide. The survival time was measured from the administration of potassium cyanide to the last breathing movement. The protected condition was determined according to the method described for anoxic asphyxia.

4. Hypobaric hypoxia in SHR rats

The rats were placed to a 6-liter exsiccator 1 hour after pretreatment to each exsiccator 2 rats were placed. The pressure was reduced in the exsiccator within 20 seconds to 22.66 kPa (170 Hgmm) and the survival time was measured from this time on until the last breathing movement. Animals which survived by 30 percent longer than the average survival of the control group were considered as protected. From the percentage of the protected animals the $ED_{50}$ i.e. the 50% effective dosage was calculated by probit analysis with the pertaining 95% fiducial limit. Our results are summarized in the following table.

TABLE

| | $ED_{50}$ (mg/kg) p.o. (95% fiducial limit) | | | |
|---|---|---|---|---|
| Compound | asphyxial anoxia | hypobaric hypoxia | cytotoxic hypoxia | hypobaric hypoxia SHR |
| 0207724 | 50.0 | 27.5 (13.7–53.6) | 17.5 (11.0–22.8) | 8.2 (4.1–11.3) |
| Vincamin | 51.1 | 60.7 (28.4–85.1) | 27.0 (15.2–42.1) | 27.9 (14.1–50.3) |
| Piracetam | 100.0 | 100.0 | 131.5 (95.9–208.1) | 293.0 (150.1–300.1) |

Code number 0207724 stands for 3-(4-phenyl-1,2,3,6-tetra-hydro-1-pyridyl)-1-[4-(4-chloro-benzyl)-phenyl]-1-propanol.

For testing the active ingredients various forms of hypoxia were used. In case of asphyxial anoxia the complete loss of the oxygen supply, at hypobaric hypoxia the reducing of the oxygen saturation condition of the haemoglobin and in case of cytotoxic hypoxia the blocking of the mytochondrial breathing enzyme cause a functional disorganisation and necrosis of the cells, even death in otherwise healthy mice. The spontaneous hypertensive rats are more sensitive to the hypoxial influences than the normotensive animals as the survival chance of a person suffering from hypertension is also worse after suffering from hypoxial influences.

As a reference substance vincamine [(+)-14β-hydroxy-14α-methoxy-carbonyl-14,15-dihydro-eburnamenine] and piracetam [2-oxo-1-pyrrolidinyl-acetic amide] were used. Vincamine increases the oxygen supply (vasodilator) and modulates the metabolic processes of the brain (cerebro-protective), while piracetam mainly improves the adaptation capability of the brain in pathologic conditions.

In all hypoxic models used in our experiments vincamin proved to be effective, the survival time of the animals was prolonged. The antihypoxic effect of piracetam could be proved on two models, although the dosage was by 5–10 times higher than that of vincamine.

The antihypoxic activity of the compound according to the invention was twice as high than that of vincamine on all models on which the tolerance of healthy animals was tested against hypoxic influences. By using cytotoxic hypoxia not only the survival time was prolonged but also a significant preventive activity could be observed. 40 percent of the animals survived the insult. This proved that the activity is also qualitatively different from that of the reference substance. It is particularly preferable that the antihypoxic activity of the compound is most significant in hypertensive animals as the background cause of primary vascular dementias and of degenerative processes can be seen in the pathological alterations of the metabolism.

The active ingredients of the formula (I) can be converted to pharmaceutical compositions by admixing same with pharmaceutically acceptable non-toxic inert solid or liquid carriers and/or excipients which ar suitable for parenteral or enteral administration. As carriers e.g. water, gelatine, lactic sugar, starch, pectin, magnesium stearate, talc, vegetable oils, such as peanut oil, olive oil etc. can be used. The active ingredient can be finished into conventional pharmaceutical compositions, such as in solid state, i.e. rounded and angular tablets, dragées, capsules, such as gelatine capsules, pilules or suppositories. The amount of the solid active ingredients within a unit of the pharmaceutical composition such as tablet, capsule or unit solution etc. can vary within a wide range, preferably within 25 mg and 1 g. The compositions can optionally contain the conventional pharmaceutical excipients, such as preservatives, stabilizers, wetting agents, emulsifying agents etc. The compositions may be prepared by known methods, such as in case of solid compositions by mixing, screening, granulating and compressing of the components. The compositions may be subjected to further technological operations, such as sterilization.

The dosage to be used is dependent on the body weight of the person or animal to be treated, on the reactivity and on the severeness of the condition to be influenced and on the frequency as well on the method of route of the administration of the doses. The dosage can vary within a wide range. The preferred dosage can be determined by the physician on the basis of his skilled knowledge.

SPECIFIC EXAMPLES

The further details of the invention are illustrated by the following Examples within limiting the invention to the Examples.

EXAMPLE 1

3-(4-Phenyl-1,2,3,6-tetrahydro-1-pyridyl)-1-[4-(4-chloro-benzyl)-phenyl]-1-propanol 0.4 g (0.01 mole) of sodium hydroxide are dissolved in 30 ml of methanol whereafter 0.01 mole of 3-(4-phenyl-1,2,3,6-tetrahydro-1-pyridyl)-1-[4-(4-chloro-benzyl)-phenyl]-1-propanone hydrochloride is added to the solution. To the suspension thus obtained 0.4 g (0.04 mole) of sodium-tetrahydrido-borate] is added at 10° C. within 15 minutes, whereafter the reaction mixture is stirred for 20 minutes at room temperature. The reduction can be monitored by thin layer chromatography. As a developing agent a mixture of hexane-dioxane (3:2) can be used. When the reaction is over, the mixture is poured into 150 ml of water and the product is filtered after stirring for 15 minutes and the mixture is washed with 20 ml of water. The nutsch wet compound is recrystallized from isopropanol. The named compound is obtained with a yield of 93.24%. Melting point: 95°–97° C.

The corresponding propanone derivatives of the general formula (II) are used and the following compounds can be prepared by the method described above. The hydrochloride salts are prepared from the corresponding base with ethanolic hydrochloride solution:

3-[4-(4-fluoro-phenyl)-1,2,3,6-tetrahydro-1-pyridyl]-1-[4-(4-chloro-benzyl)-phenyl]-1-propanol, yield: 96.27%, m.p.: 98°–102 ° C.;

3-[4-(4-chloro-phenyl)-1,2,3,6-tetrahydro-1-pyridyl]-1-[4-(4-chloro-benzyl)-phenyl]-1-propanol, yield: 80.72%, m.p.: 123°–124° C.;

3-[4-(3-trifluoro-methyl-phenyl)-1,2,3,6-tetrahydro-1-pyridyl]-1-[4-(4-chloro-benzyl)-phenyl]-1-propanol, yield: 76.06%, m.p.: 89°–92° C.;

3-(4-phenyl-1,2,3,6-tetrahydro-1-pyridyl)-1-(4-benzyl-phenyl)-1-propanol-hydrochloride, yield: 66.21%, mp.: 210°–212° C.;

3-[4-(4-fluoro-phenyl)-1,2,3,6-tetrahydro-1-pyridyl]-1-(4-(4-benzyl-phenyl)-1-propanol-hydrochloride, yield: 67.65%, m.p.: 195°–197° C.;

3-[4-(4-chloro-phenyl)-1,2,3,6-tetrahydro-1-pyridyl]-1-(4-benzyl-phenyl)-1-propanol, yield: 96.0%, m.p.: 92°–96° C.;

3-[4-(3-trifluoro-methyl-phenyl)-1,2,3,6-tetrahydro-1-pyridyl]-1-(4-benzyl-phenyl)-1-propanol-hydrochloride, yield: 65.00; m.p.: 207°–211° C.;

3-(4-phenyl-1,2,3,6-tetrahydro-1-pyridyl)-1-(4-(2-chloro-benzyl)-phenyl)-1-propanol, yield: 82.5%, m.p.: 120°–122° C.

EXAMPLE 2

3-(4-Phenyl-1,2,3,6-tetrahydro-1-pyridyl)-1-(1,1-biphenyl-4-yl)-1-propanol 0.4 g (0.01 mole) of sodium hydroxide are dissolved in 30 ml methanol. To the solution 30 ml of acetonitrile and 0.01 mole 3-(4-phenyl-1,2,3,6-tetrahydro-1-pyridyl)-1-(1,1-biphenyl-4-yl)-1-propanone-hydrochloride is added. The solution is stirred for 15 minutes, whereafter 0.8 g (0.2 mole) of sodium-[tetrahydridoborate] is added. The solution is stirred for 15 minutes, whereafter 0.8 (0.02 mole) of sodium-[tetrahydridoborate] is added. The mixture is stirred at room temperature for 30 minutes, whereafter the reaction mixture is analyzed by thin layer chromatography (Developing agent: a mixture of hexane-dioxane=3:2). When the reaction is completed the mixture is poured into 150 ml of water and the crude 3-(4-phenyl-1,2,3,6-tetrahydro-1-pyridyl)-1-(1,1-biphenyl-4-il)-1-propanol base is filtered off after stirring for 10 minutes. The mixture is washed with 20 ml of water and recrystallized from methanol. Yield: 65.54%. M.p.: 133°–135 ° C.

By using the corresponding propanone derivatives as described above the following compounds can be prepared. The hydrochloric salt is prepared from the corresponding base by using ethanolic hydrochloride solution:

3-[4-(4-Fluoro-phenyl)-1,2,3,6-tetrahydro-I-pyridyl]-1-(1,1-biphenyl-4-yl)-1-propano]-hydrochloride, yield: 93.67%, m.p.: 234°–235 ° C.;

3-[4-(4-chloro-phenyl)-1,2,3,6-tetrahydro-1-pyridyl]-1-(1,1-biphenyl-4-yl)-1-propanol, yield: 87.62%, m.p.: 183°–186 ° C.;

3-[4-(3-trifluor-methyl-phenyl)-1,2,3,6-tetrahydro-1-pyridyl]-1-(1,1-biphenyl-4-yl)-1-propanol, yield: 95.00%, m.p.: 219°–221° C.;

3-(4-phenyl-1,2,3,6-tetrahydro-1-pyridyl)-1-[4-(4-chloro-phenyl)-phenyl]-propanol, yield: 52.79%, m.p.: 155°–156 ° C.;

3-[4-(4-fluoro-phenyl)-1,2,3,6-tetrahydro-1-pyridyl]-1-[4-(4-chloro-phenyl)-phenyl]-propanol, yield: 94.80%, m.p.: 153°–157 ° C.;

3-[4-(4-chloro-phenyl)-1,2,3,6-tetrahydro-1-pyridyl]-1-[4-(4-chloro-phenyl)-phenyl]-propanol, yield: 89.94%, m.p.: 165°–169 ° C.;

3-[4-(3-trifluoro-methyl-phenyl)-1,2,3,6-tetrahydro-1-pyridyl]-1-[4-(4-chloro-phenyl)-phenyl]-propanol, yield: 85.94%, m.p.: 104°–108 ° C.;

3-(4-phenyl-1,2,3,6-tetrahydro-1-pyridyl)-1-[4-(4-bromophenyl)-phenyl]-propanol,, yield: 74.59%, m.p.: 156°–157 ° C.;

3-[4-(4-fluoro-phenyl)-1,2,3,6-tetrahydro-pyridyl]-1-[4-(4-bromo-phenyl)-phenyl]-propanol, yield: 72.00%, m.p.: 161°–163 ° C.;

3-[4-(4-chloro-phenyl)-1,2,3,6-tetrahydro-1-pyridyl]-1-[4-(4-bromo-phenyl)-phenyl]-propanol, yield: 79.46%, m.p.: 168°–173 ° C.;

3-(4-phenyl-1,2,3,6-tetrahydro-1-pyridyl)-1-[4-(4-fluoro-phenyl)-phenyl]-propanol, yield: 69.58%, m.p. 149°–151 ° C.;

3-[4-(4-fluoro-phenyl)-1,2,3,6-tetrahydro-1-pyridyl]-1-[4-(4-fluoro-phenyl)-phenyl]-propanol, yield: 86.39%; m.p.: 142°–144 ° C.;

3-[4-(4-chloro-phenyl)-1,2,3,6-tetrahydro-1-pyridyl]-1-[4-(4-fluoro-phenyl)-phenyl]-propanol, yield: 66.47%; m.p.: 175°–178 ° C.

EXAMPLE 3

3-(4-Phenyl-1,2,3,6-tetrahydro-1-pyridyl)-1-[4-(4-1-chloro-phenyl)-phenyl]-2-methyl-propanol and hydrochloride thereof 0.18 g (4.4 mmole) of sodium-hydroxide are dissolved in 10 ml of methanol and 30 ml of acetonitrile and 1.95 g (4.4 mmole) of 3-(4-phenyl-1,2,3,6-tetrahydro-pyridyl)-1-[4-(4-chloro-phenyl)-phenyl]-2-methyl-propanone-hydrochloride are added to the solution. The solution is then stirred for 15 minutes, whereafter 0.3 g (8 mmole) of sodium-[tetrahydrido borate] are added at 10° C. The mixture is stirred for 5 hours at 40° C. and the reduction is monitored by thin layer chromatography. As a developing agent a 4:1 volume ratio benzene-methanol mixture can be used, which is acidified with 1 drop of 1 N hydrochloric acid solution. When the reaction is completed the mixture is poured onto 150 ml water and after 10 minutes of stirring the named compound obtained in the form of a free base is filtered off, washed with 20 ml of water and recrystallized from methanol. Yield: 1.67 g (90.9%). M.p.: 140°–141° C.

1.2 g free base as obtained above is dissolved in 10 ml of chloroform and acidified to pH 2 by using an ethanolic hydrochloride solution. The solution is evaporated and recrystallized from ether. Yield: 1.07 g of hydrochloride of the title compound. M.p.: 171°–173° C.

EXAMPLE 4

The preparation of the tablets is demonstrated by the following Examples:

| a) 150 mg tablets containing 5 mg active ingredient | g |
| --- | --- |
| active ingredient | 5 |
| gelatin | 3 |
| magnesium stearate | 2 |
| talc | 5 |
| potato starch | 40 |

| | |
|---|---|
| lactose | 95 |
| b) 300 mg tablets, containing 50 mg active ingredient | g |
| active ingredient | 50 |
| polyvidone | 6 |
| magnesium-stearate | 3 |
| talc | 9 |
| potato starch | 84 |
| lactose | 148 |

The powder mixture as given under a) and b) is subjected to wet granulation and compression and 150 and 300 mg tablets are compressed. Each of the above tablets contains 5 and 50 mg, respectively,, active ingredient.

We claim:

1. A compound of the formula (I)

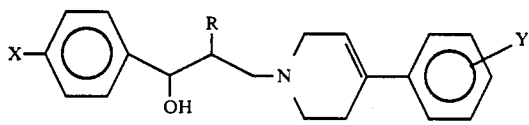

wherein

R stands for hydrogen or an alkyl group,

X stands for an unsubstituted phenyl or benzyl group or for a phenyl or benzyl group substituted with a halogen atom, Y stands for hydrogen or halogen or a trifluoromethyl group or an enantiomer or an acid addition salt thereof.

2. 3-(4-Phenyl-1,2,3,6-tetrahydro-1-pyridyl)-1-[4-(4-chloro-benzyl)-phenyl]-1-propanol or an acid addition salt thereof as defined in claim 1.

3. 3-[4-(4-Fluoro-phenyl-1,2,3,6-tetrahydro-1-pyridyl)-1-[4-(4-chloro-benzyl)-phenyl]-1-propanol or an acid addition salt thereof as defined in claim 1.

4. 3-[4-(4-Chloro-phenyl-1,2,3,6-tetrahydro-1-pyridyl)-1-[4-(4-chloro-benzyl)-phenyl]-1-propanol or an acid addition salt thereof as defined in claim 1.

5. 3-[4-(3-Trifluoro-methyl-phenyl)-1,2,3,6-tetrahydro-1-pyridyl)-1-[4-(4-chloro-benzyl)-phenyl]-1-propanol or an acid addition salt thereof as defined in claim 1.

6. 3-(4-Phenyl)-1,2,3,6-tetrahydro-1-pyridyl)-1-[4-(4-benzyl)-phenyl]-1propanol or an acid addition salt thereof as defined in claim 1.

7. 3-[4-(4-Fluor-phenyl)-1,2,3,6-tetrahydro-1-pyridyl)-1-[4-(4-benzyl)-phenyl]-1-propanol or an acid addition salt thereof as defined in claim 1.

8. 3-[4-(4-Chloro-phenyl)-1,2,3,6-tetrahydro-1-pyridyl)-1-[4-(4-benzyl)-phenyl]-1-propanol or an acid addition salt thereof as defined in claim 1.

9. 3-[4-(3-Trifluoro-methyl-phenyl)-1,2,3,6-tetrahydro-1-pyridyl)-1-[4-(4-benzyl)-phenyl]-1-propanol or an acid addition salt thereof as defined in claim 1.

10. 3-(4-Phenyl-1,2,3,6-tetrahydro-1-pyridyl)-1-[4-(2-chloro-benzyl)-phenyl]-1-propanol or an acid addition salt thereof as defined in claim 1.

11. 3-(4-Phenyl-1,2,3,6-tetrahydro-1-pyridyl)-1-(1,1-biphenyl-4-il)-1-propanol or an acid addition salt thereof as defined in claim 1.

12. 3-[4-(4-Fluor-phenyl)-1,2,3,6-tetrahydro-1-pyridyl]-1-(1,1-biphenyl-4-il)-1-propanol or an acid addition salt thereof as defined in claim 1.

13. 3-[4-(4-Chloro-phenyl)-1,2,3,6-tetrahydro-1-pyridyl]-1-(1,1-biphenyl-4-il)-1-propanol or an acid addition salt thereof as defined in claim 1.

14. 3-[4-(3-Trifluoro-methyl-phenyl)-1,2,3,6-tetrahydro-1-pyridyl]-1-[1,1-biphenyl-4-il)1-propanol or an acid addition salt thereof as defined in claim 1.

15. 3-(4-Phenyl-1,2,3,6-tetrahydro-1-pyridyl)-1-[4-(4-chloro-phenyl)-phenyl]-propanol or an acid addition salt thereof as defined in claim 1.

16. 3-[4-(4-Fluoro-phenyl)-1,2,3,6-tetrahydro-1-pyridyl]-1-[4(4-chloro-phenyl)-phenyl]-propanol or an acid addition salt thereof as defined in claim 1.

17. 3-[4-(4-Chloro-phenyl)-1,2,3,6-tetrahydro-1-pyridyl)-1-[4-(4-chloro-phenyl)-phenyl]-propanol or an acid addition salt thereof as defined in claim 1.

18. 3-[4-(3-Trifluoro-methyl-phenyl)-1,2,3,6-tetrahydro-1-pyridyl]-1-[4(4-chloro-phenyl)-phenyl]-propanol or an acid addition salt thereof as defined in claim 1.

19. 3-(4-Phenyl-1,2,3,6-tetrahydro-1-pyridyl)-1-[4-(4-bromo-phenyl)-phenyl]-propanol or an acid addition salt thereof as defined in claim 1.

20. 3-[4-(4-Fluoro-phenyl)-1,2,3,6-tetrahydro-1-pyridyl]-1-[4(4-bromo-phenyl)-phenyl]-propanol or an acid addition salt thereof as defined in claim 1.

21. 3-[4-(4-Chloro-phenyl)-1,2,3,6-tetrahydro-1-pyridyl]-1-[4-(4-bromo-phenyl)-phenyl]-propanol or an acid addition salt thereof as defined in claim 1.

22. 3-(4-Phenyl-1,2,3,6-tetrahydro-1-pyridyl)-1-[4-(4-fluoro-phenyl)-phenyl]-propanol or an acid addition salt thereof as defined in claim 1.

23. 3-[4-(4-Fluoro-phenyl)-1,2,3,6-tetrahydro-1-pyridyl]-1-[4(4-fluoro-phenyl)-phenyl]-propanol or an acid addition salt thereof as defined in claim 1.

24. 3-[4-(4-Chloro-phenyl)-1,2,3,6-tetrahydro-1-pyridyl]-1-[4-(4-fluoro-phenyl)-phenyl]-propanol or an acid addition salt thereof as defined in claim 1.

25. 3-(4-Phenyl-1,2,3,6-tetrahydro-1-pyridyl)-1-[4-(4-chloro-phenyl)-phenyl]-2-methyl-propanol or an acid addition salt thereof as defined in claim 1.

26. Pharmaceutical compositions for improving blood circulation in the brain in order to produce antihypoxic effects, and to influence memory disturbances caused by hypoxia which comprises as an active ingredient a 1,2,3,6-tetrahydropyridin derivative as defined in claim 1.

27. Method of treatment of mammals including humans in order to improve blood circulation in the brain, in order to produce antipypoxic effects and to influence memory disturbances caused by hypoxia which comprises administration of a 1,2,3,6-tetrahydropyridin derivative as given in claim 1 in a therapeutically effective dose to the organism of the person or animal to be treated in pure state or in the form of a pharmaceutical composition containing said compound as active ingredient.

* * * * *